United States Patent [19]
Hashimoto et al.

[11] Patent Number: 5,307,816
[45] Date of Patent: May 3, 1994

[54] THROMBUS RESOLVING TREATMENT APPARATUS

[75] Inventors: Shinichi Hashimoto, Kawasaki; Shiroh Saitoh, Yokohama; Katsuhiko Fujimoto, Kawasaki; Satoshi Aida, Tokyo, all of Japan

[73] Assignee: Kabushiki Kaisha Toshiba, Kawasaki, Japan

[21] Appl. No.: 932,952

[22] Filed: Aug. 21, 1992

[30] Foreign Application Priority Data

Aug. 21, 1991 [JP] Japan .................................. 3-209446
Sep. 13, 1991 [JP] Japan .................................. 3-261387

[51] Int. Cl.$^5$ .............................................. A61B 8/00
[52] U.S. Cl. ........................ 128/660.03; 128/662.06
[58] Field of Search ................. 128/660.03, 660.07, 128/662.05, 662.06

[56] References Cited

U.S. PATENT DOCUMENTS 5,158,088 10/1992 Nelson et al. ............... 128/662.06 X
5,161,536 11/1992 Vilkomerson et al. .... 128/662.05 X
5,203,337 4/1993 Feldman ........................ 129/662.06
5,213,102 5/1993 Kudo et al. .................... 128/660.03

FOREIGN PATENT DOCUMENTS 2-126848 5/1990 Japan.

OTHER PUBLICATIONS

Circulation 80: 11-345, 1989, Sumihiko Kudo, et al., "Noninvasive Thrombolysis with Ultrasound."

Primary Examiner—Francis Jaworski
Attorney, Agent, or Firm—Oblon, Spivak, McClelland, Maier & Neustadt

[57] ABSTRACT

A thrombus resolving treatment apparatus of this invention has an ultrasonic radiator for radiating a therapeutic ultrasonic wave to a thrombus portion, an ultrasonic probe for obtaining B mode image data of an interior of a patient's body, a first ultrasonic imaging unit for visually displaying the B mode image data supplied from the ultrasonic probe, a catheter inserted in the blood vessel, an ultrasonic transducer, provided to the catheter, for obtaining cross-sectional image data of an interior of a blood vessel, and a second ultrasonic imaging unit for visually displaying the cross-sectional image data supplied from the ultrasonic transducer.

9 Claims, 9 Drawing Sheets

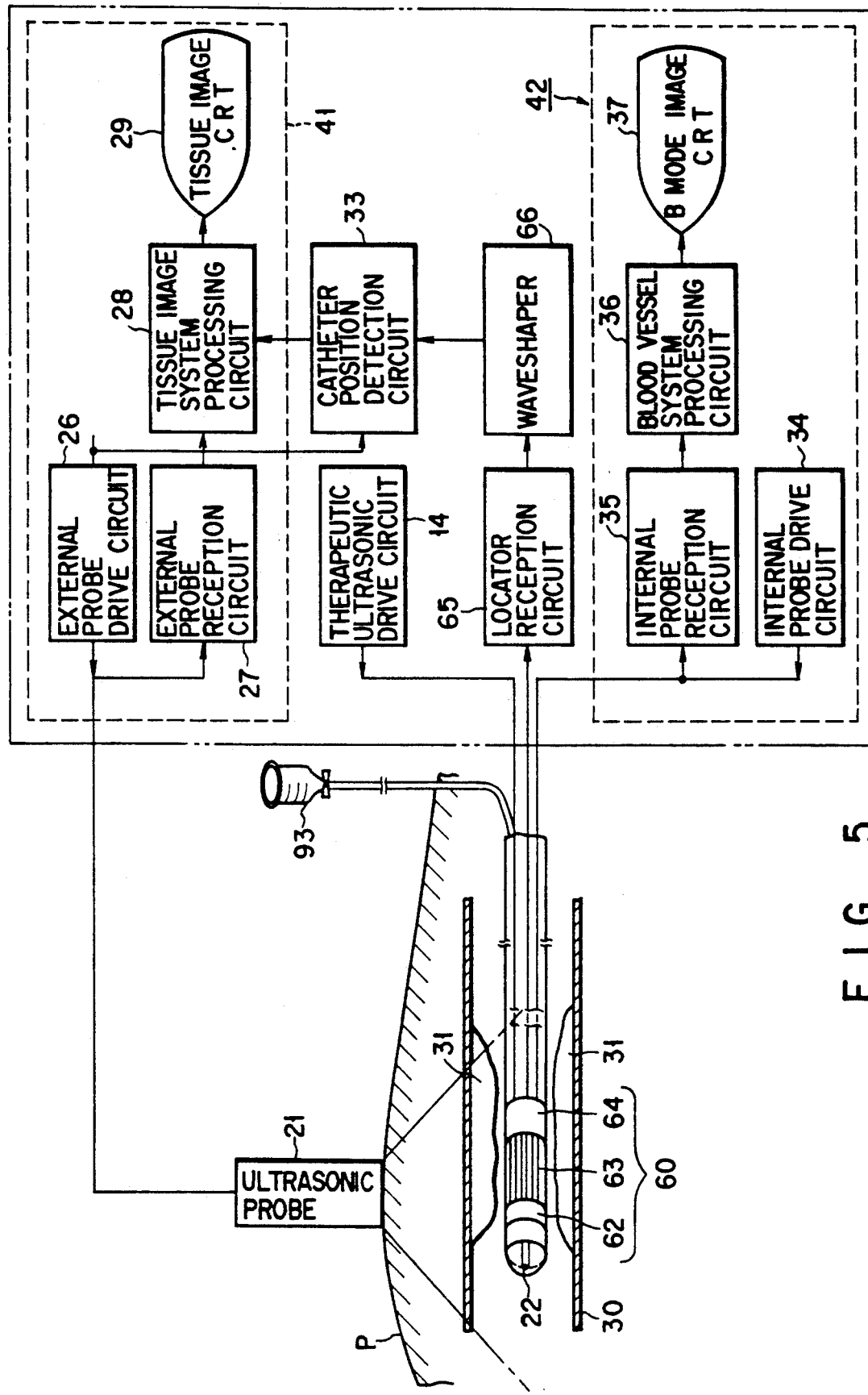
F I G. 5

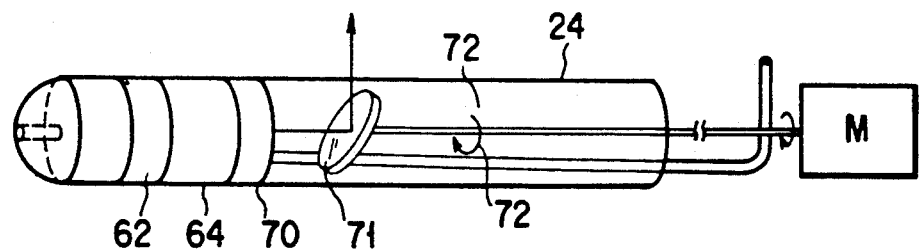
F I G. 6
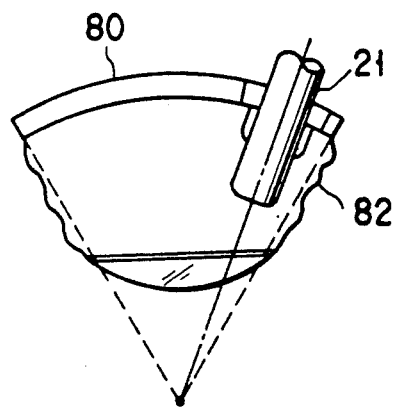
F I G. 10
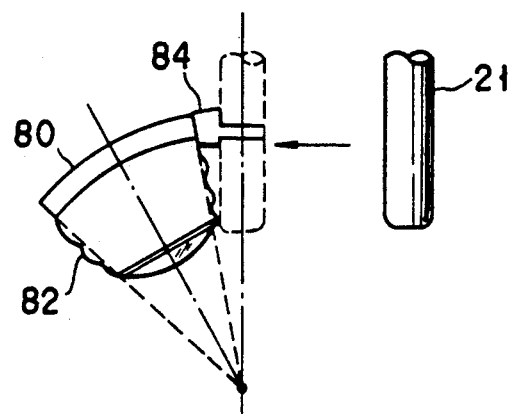
F I G. 11

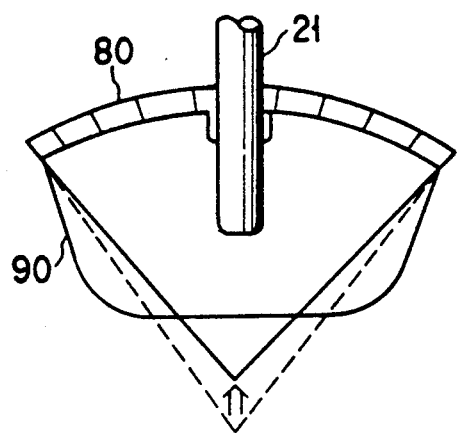
F I G. 12
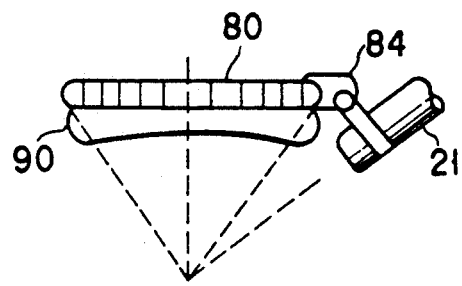
F I G. 13
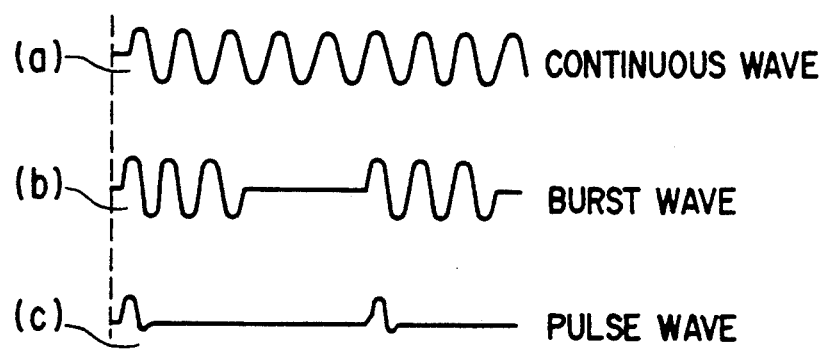
F I G. 14

THROMBUS RESOLVING TREATMENT APPARATUS

BACKGROUND OF THE INVENTION

1. Field of the Invention

The present invention relates to a thrombus resolving treatment apparatus for resolving a thrombus formed in a blood vessel by using a thrombus resolvent and an ultrasonic wave.

2. Description of the Related Art

In Europe and the U.S., vascular diseases, e.g., arteriosclerosis and thrombosis, have been found very often and are increasing. In Japan as well, thrombotic ischemic heart diseases, e.g., cerebral infarction and myocardial infarction, are increasing due to the change in diet and are listed as one of the two major causes of death (the other cause is a cancer). To treat such an ischemic heart disease, a thrombectomy must be performed. The thrombectomy or vascular grafting is highly invasive to the patient's body and thus is not appropriate especially for an aged patient prone to suffer from this type of disease. A thrombus formed in a cerebral blood vessel or a cardiac coronary artery causes the infarction of cerebral or myocardial cells unless a thrombectomy is immediately performed. In particular, the former can endanger the life or cause a serious aftereffect if the thrombectomy is retarded. Hence, it is required to perform the thrombectomy as quickly as possible.

For example, thrombus resolving treatments, e.g., PTCR (percutaneous transluminal coronary recanalization), "intravenous drip", (a technique to administer a large amount of thrombus resolvent having a high concentration by drip over a long period of time), "intraarterial infusion" (a technique to administer a thrombus resolvent to a carotid through a catheter), and PTCA (percutaneous transluminal coronary angioplasty) attract attention as quick, effective thrombus treatments that are less invasive to the patient's body when compared to a surgical operation or the like. Of these treatments, according to PTCR, a catheter is inserted in a coronary artery, and a thrombus resolvent is quickly injected into the coronary artery close to the thrombus while the positions of the blood vessel and the catheter are fluoroscopically monitored by using an X-ray contrast medium. With PTCR, however, the recanalization rate of the blood vessel is low, and the problem of X-ray exposure exists. In "intravenous drip", although the blood vessel recanalization rate is comparatively high, a side effect occurs that the blood becomes hard to coagulate because of the large amount of thrombus resolvent. Furthermore, according to PTCA, the inner wall of the blood vessel is flexibly expanded by a balloon catheter. Hence, although the "blood vessel recanalization rate" is high, a thrombus reoccurrence rate is high.

Recently, the effect of the thrombus resolvent is increased by adopting both administration of the thrombus resolvent by "intravenous drip" and external ultrasonic radiation to the thrombus. Since the administration amount of the thrombus resolvent can be decreased with this method, the side effects are reported to decrease (*Medical Electronics and Bioengineering*, vol. 26, page 536, 1988). Even with this method, however, it is preferable to minimize the administration amount of the thrombus resolvent. For this purpose, a therapeutic ultrasonic wave must be efficiently radiated on a thrombus portion, and the effect of the thrombus resolving treatment must be monitored so that no excessive thrombus resolvent may be administered once the thrombus is completely resolved. It is also preferable that the effect of the thrombus resolving treatment can be quantitatively identified in order to perform a precise, efficient treatment.

As described above, the thrombus resolving treatment method that adopts both administration of the thrombus resolvent and ultrasonic radiation is advantageous in that it has in principle a high therapeutic effect and has a few side effects. In order to exhibit its advantage to the maximum, the therapeutic ultrasonic wave must be efficiently and precisely radiated on a thrombus portion as the diseased part, and the thrombus therapeutic effect must be monitored so that no excessive thrombus resolvent may be administered. Preferably, the treatment must be performed while precisely identifying the therapeutic effect.

SUMMARY OF THE INVENTION

It is an object of the present invention to provide a thrombus resolving treatment apparatus, when resolving and treating a thrombus by adopting both administration of a thrombus resolvent and ultrasonic radiation, which can efficiently radiate a therapeutic ultrasonic wave and monitor the effect of thrombus resolving treatment in order to obtain a high therapeutic effect and minimize the administration amount of the thrombus resolvent, thus minimizing side effects.

In order to achieve the above object, according to the present invention, there is provided a thrombus resolving treatment apparatus for resolving a thrombus by radiating a therapeutic ultrasonic wave to a thrombus portion in a blood vessel in which a thrombus resolvent is injected, comprising an ultrasonic radiator for radiating a therapeutic ultrasonic wave to the thrombus portion, an ultrasonic probe for obtaining tomographic image data of an interior of a patient's body, a first ultrasonic imaging unit for visually displaying the tomographic image data supplied from the ultrasonic probe, a catheter inserted in the blood vessel, an ultrasonic transducer, provided to the catheter, for obtaining tomographic image data of an interior of the blood vessel, and a second ultrasonic imaging unit for visually displaying the tomographic image data supplied from the ultrasonic transducer.

According to the present invention, there is also provided a thrombus resolving treatment apparatus in which, in addition to the basic structure as described above, the ultrasonic transducer is imparted with a function of detecting an ultrasonic wave supplied from the ultrasonic probe, and which has a position detection means for detecting a position of the catheter by processing a detection signal supplied from the ultrasonic probe which is output from the ultrasonic transducer, and a means for displaying a detection result of the position detection means on a display screen of the first ultrasonic imaging unit.

In this case, the ultrasonic transducer is preferably constituted by at least one strip-shaped piezoelectric element provided in the longitudinal direction of the catheter. Two of the thickness of the piezoelectric element, its length in the circumferential direction of the catheter, and its length in the axial direction of the catheter correspond to a frequency of the ultrasonic wave for obtaining the tomographic image data of the blood vessel and a frequency of the ultrasonic wave used by the ultrasonic probe to obtain the tomographic image data of the interior of the patient. It is preferable that the remaining one of the thickness, the length in the circumferential direction of the catheter, and the length in the axial direction of the catheter corresponds to the frequency of the ultrasonic wave radiated by the ultrasonic radiator.

Furthermore, in addition to the basic structure described above, the present invention may also comprise a calculation means for calculating a value representing the effect of the thrombus resolving treatment on the basis of the tomographic image data supplied from the ultrasonic transducer, and a means for stopping radiation of the therapeutic ultrasonic wave from the ultrasonic radiator when the value calculated by the calculation means has reached a predetermined value. The present invention may also comprise a means for stopping injection of the thrombus resolvent into the blood vessel when the value calculated by the calculation means has reached the predetermined value.

In the first ultrasonic imaging unit, for example, a B mode tomographic image is displayed as the tomographic image of the interior of the patient's body, and the thrombus portion can be obtained from this display. In the second ultrasonic imaging unit, a cross-sectional tomographic image is displayed as the tomographic image of the blood vessel, and the state of the thrombus resolving treatment can be obtained from this display. Accordingly, the therapeutic ultrasonic wave can be radiated precisely on the thrombus portion to improve the therapeutic effect, and when the thrombus is sufficiently resolved, excessive administration of the thrombus resolvent is prevented to avoid undesirable side effects. That is, the position of the thrombus which cannot be easily seen from the ultrasonic simple B mode image can be correctly obtained to avoid excessive radiation of the therapeutic ultrasonic wave.

The value representing the thrombus therapeutic effect, e.g., "the recanalization rate" is obtained by calculation. If radiation of the therapeutic ultrasonic wave by the ultrasonic radiator is stopped or furthermore if injection of the thrombus resolvent into the thrombus is stopped when this value has reached a predetermined value, the treatment can be automatically stopped as soon as the thrombus is sufficiently resolved. As a result, a more efficient treatment having less side effects can be performed.

Furthermore, in the present invention, the ultrasonic wave from the ultrasonic probe is detected by the ultrasonic transducer, the position of the catheter, i.e., the distance and direction from the ultrasonic probe are detected by processing the detection signal, and the detection result is displayed on the first ultrasonic imaging unit to be superposed on the tomographic image of the interior of the patient's body, thus allowing confirmation as to whether the catheter is correctly inserted in the thrombus portion. In this case, regarding the strip-shaped piezoelectric element provided along the longitudinal direction of the catheter to constitute the ultrasonic transducer, if any two of its thickness, its length in the circumferential direction of the catheter, and its length in the axial direction of the catheter are set to correspond to the frequency of the ultrasonic wave for obtaining the tomographic image data of the blood vessel and the frequency of the ultrasonic wave used by the ultrasonic probe to obtain the tomographic image data of the interior of the patient's body, the piezoelectric element can perform two functions, i.e., a function of monitoring the tomographic image of the blood vessel and a function of notifying the position of the catheter, i.e., the position of the ultrasonic transducer itself. When these two functions are combined, the number of piezoelectric elements constituting the ultrasonic transducer can be decreased, resulting in a simple, small ultrasonic transducer that can be easily mounted on the catheter. When the remaining one of the thickness, the length in the circumferential direction of the catheter, and the length in the axial direction of the catheter, of the piezoelectric element is set to correspond to the frequency of the ultrasonic wave radiated by the ultrasonic radiator, the ultrasonic transducer can be imparted with a function of monitoring the radiation position of the therapeutic ultrasonic wave by the ultrasonic radiator.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of is the invention.

FIG. 5 is a view showing the structure of a thrombus resolving treatment apparatus according to the third embodiment of the present invention;

FIG. 6 is a perspective view of an ultrasonic transducer according to the fourth embodiment of the present invention;

FIG. 10 is a view showing another example of the mounting state of an ultrasonic probe to an ultrasonic radiator;

FIG. 11 is a view showing still another example of the mounting state of an ultrasonic probe to an ultrasonic radiator;

FIG. 12 is a view showing another arrangement of the ultrasonic radiator;

FIG. 13 is a view showing still another arrangement of the ultrasonic radiator;

FIGS. 14(a), 14(b), and 14(c) show various drive waveforms of the ultrasonic radiator;

DETAILED DESCRIPTION OF THE PREFERRED EMBODIMENTS

Figure 1:
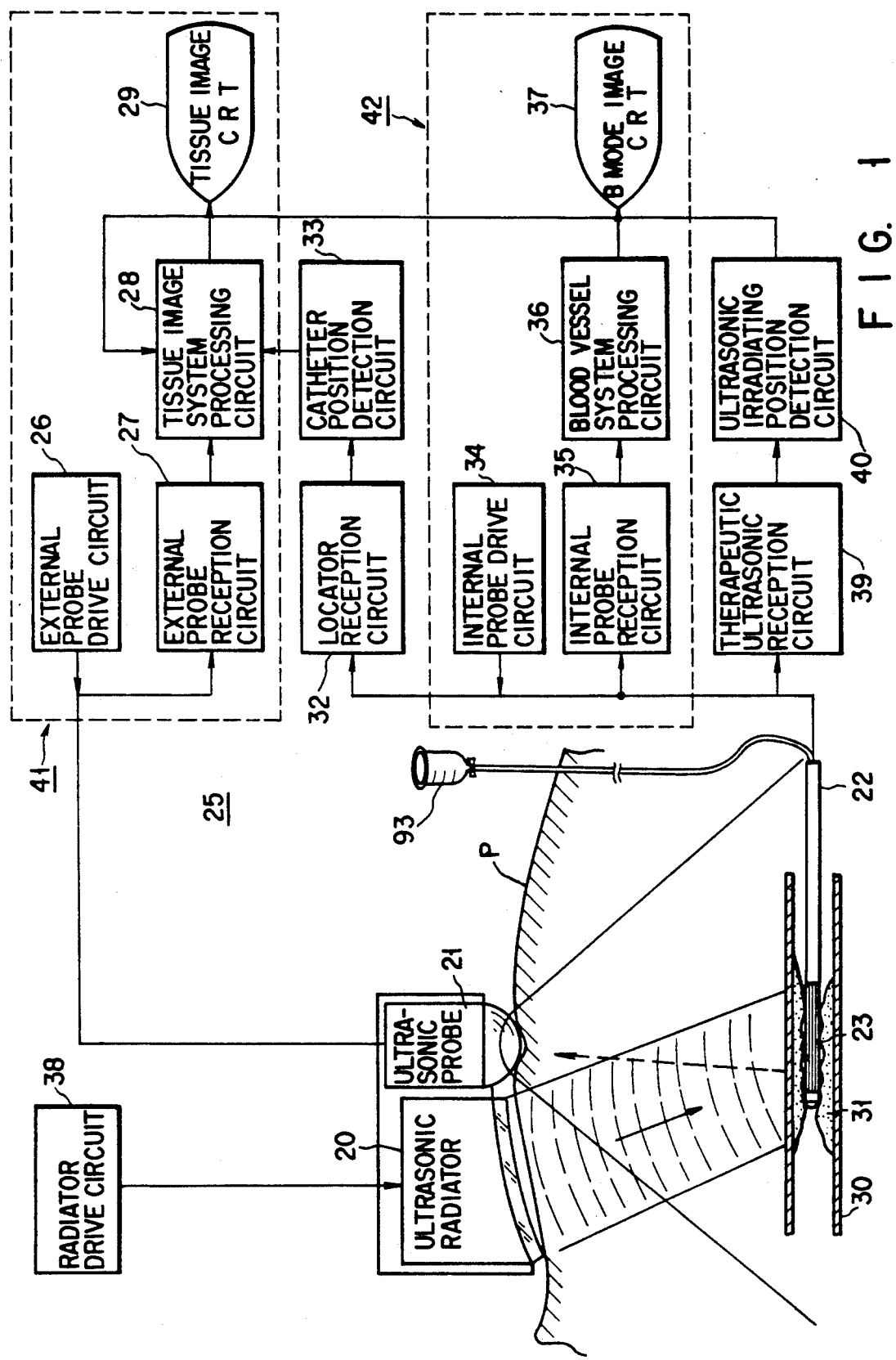
FIG. 1 is a view showing the structure of a thrombus resolving treatment apparatus according to the first embodiment of the present invention.

FIG. 1 is a view showing the structure of a thrombus resolving treatment apparatus according to the first embodiment of the present invention. This thrombus resolving treatment apparatus has an ultrasonic radiator 20 for externally radiating a therapeutic ultrasonic wave on a thrombus portion, an ultrasonic probe 21 for externally monitoring a thrombus position, a catheter 22 percutaneously inserted to the thrombus position, an ultrasonic transducer 23 mounted on the circumferential surface of the distal end of the catheter 22, and a system body 25. The system body 25 is connected to the ultrasonic radiator 20, the ultrasonic probe 21, and the ultrasonic transducer 23, to visualize tomographic image data obtained by the ultrasonic probe 21 and tomographic image data of a cross section of a blood vessel obtained by the ultrasonic transducer 23, to display the position of the ultrasonic transducer 23, and to control an ultrasonic wave to be radiated on the thrombus.

More specifically, the ultrasonic radiator 20 radiates a therapeutic ultrasonic wave having a frequency of 50 kHz to 1 MHz (e.g. 450 kHz) from the outside of a patient P to a thrombus 31 upon reception of a drive signal supplied from a radiator drive circuit 38 in the system body 25. The catheter 22 incorporates a thrombus resolvent injection tube to be connected to a thrombus resolvent injection controller (not shown) in the system body 25. Thus, the thrombus 31 is resolved and treated by adopting both administration of the thrombus resolvent and radiation of the therapeutic ultrasonic wave.

The ultrasonic probe 21 comprises a vibrator array constituted by aligning a plurality of ultrasonic vibrators in a row and is provided in tight contact with the body surface of the patient P. The interior of the patient P is sector-scanned (the scanning scope is a fan-shaped portion in FIG. 1) when drive signals are supplied from an external probe drive circuit 26 in the system body 25 at predetermined relative delay time intervals. The frequency of the ultrasonic wave received and transmitted by the ultrasonic probe 21 is, e.g., 5 MHz. The ultrasonic wave transmitted from the ultrasonic probe 21 is reflected by an internal tissue in the patient P. The reflected wave is received by the same ultrasonic probe 21 and converted to an electrical signal (e.g., an echo signal). The echo signals obtained by the respective vibrators of the ultrasonic probe 21 are sent to an external probe reception circuit 27 in the system body 25 and are delayed by the same relative delay time intervals as that during transmission. Then, the echo signals are subjected to processing, e.g., phasing/addition, wave detection, and amplitude compression in a tissue image system processing circuit 28, and supplied to a tissue image CRT 29 to display a B mode image of the internal tissues. The external probe drive circuit 26, the external probe reception circuit 27, the tissue image system processing circuit 28, and the tissue image CRT 29 constitute a first ultrasonic imaging unit 41.

The catheter 22 is inserted at the position of the thrombus 31 formed in a blood vessel 30 of the patient P. The ultrasonic transducer 23 mounted on the distal end of the catheter 22 is used to execute the first function, i.e., to obtain the tomographic image data of the blood vessel 30 together with an internal probe drive circuit 34 and an internal probe reception circuit 35 in the system body 25. More specifically, the ultrasonic transducer 23 performs so-called "radial scanning" in the circumferential direction of the catheter 22. The ultrasonic transducer 23 comprises a plurality of strip-shaped piezoelectric elements aligned in the circumferential direction of the catheter 22. These piezoelectric elements are sequentially selectively driven by the internal probe drive circuit 23 to perform electronic radial scanning. A signal obtained by the ultrasonic transducer 23 is processed by a blood vessel B mode imaging system processing circuit 36 and sent to a blood vessel B mode imaging CRT 37 to display a radius directional cross-sectional image of the blood vessel 30. The resolving state of the thrombus 31 at this position can be obtained by observing this cross-sectional image of the blood vessel 30. The internal probe drive circuit 34, the internal probe reception circuit 35, the blood vessel B mode imaging system processing circuit 36, and the blood vessel B mode imaging CRT 37 constitute a second ultrasonic imaging unit 42. The frequency of the ultrasonic wave transmitted and received by the ultrasonic transducer 23 is different from that of the ultrasonic probe 21 and is, e.g., 20 MHz.

The ultrasonic transducer 23 serves as a locator as its second function. More specifically, the ultrasonic transducer 23 receives an ultrasonic beam transmitted from the ultrasonic probe 21 and converts it to an electrical signal. This signal is amplified and detected by a locator reception circuit 32 in the system body 25 and sent to a catheter position detection circuit 33. The catheter position detection circuit 33 detects the position of the catheter 22, i.e., the distance between the ultrasonic probe 21 and the ultrasonic transducer 23 and the direction on the basis of an output signal from the locator reception circuit 32. The detection results of the distance and direction are supplied to the tissue image system processing circuit 28 and added to the signal from the external probe reception circuit 27 in the phase-locked manner so as to be displayed on the tissue image CRT 29 as they are superposed on the B mode image of the internal tissues.

According to another embodiment, an ultrasonic transducer 23 may be connected to a locator drive circuit. In this case, the locator drive circuit is operated to generate an ultrasonic pulse signal (i.e., an upward broken arrow) phase-locked with the transmission/reception system of an ultrasonic probe 21, and this ultrasonic pulse signal is received by the ultrasonic probe 21 to display the position of the ultrasonic transducer 23, together with the B mode image of the internal tissues, on a tissue image CRT 29.

The ultrasonic transducer 23 also has a third function, i.e., it receives a therapeutic ultrasonic wave (i.e., a downward solid arrow) from the ultrasonic radiator 20. A signal obtained by the ultrasonic transducer 23 which corresponds to the therapeutic ultrasonic wave from the ultrasonic radiator 20 is amplified and detected by a therapeutic ultrasonic reception circuit 39 and sent to a radiation position detection circuit 40. The radiation position detection circuit 40 detects the radiation position of the therapeutic ultrasonic wave from the reception strength of the therapeutic ultrasonic wave. The detection result is displayed on the tissue image CRT 29 to be superposed on the internal tissue image through the tissue image system processing circuit 28.

The procedure of the treatment of this embodiment will be described.

(1) The catheter 22 is operated, while the position of the thrombus 31 in the B mode image of the internal tissues is monitored on the tissue image CRT 29, to move the ultrasonic transducer 23.

(2) Similarly, the position of the ultrasonic transducer 23 displayed on the tissue image CRT 29 is set to coincide with the position of the thrombus 31. At this time, the cross-sectional image of the blood vessel 30 including the thrombus 31 is also simultaneously observed on the blood vessel B mode imaging CRT 37.

(3) A thrombus resolvent insertion controller (not shown) is operated to discharge the thrombus resolvent (e.g., Urokinase or t-PA) from the catheter 22 into the blood vessel 30. The radiator drive circuit 38 is operated to cause the ultrasonic radiator 20 to radiate a therapeutic ultrasonic wave toward the thrombus 31. At this time, the ultrasonic radiator 20 is moved on the body surface while observing the B mode image on the tissue image CRT 29 so that the therapeutic ultrasonic wave is precisely radiated on the thrombus 31.

(4) When the thrombus 31 is confirmed to be sufficiently resolved from the blood vessel cross-sectional image on the blood vessel B mode imaging CRT 37, discharge of the thrombus resolvent from the catheter 22 is stopped by the thrombus resolvent insertion controller.

Figure 2:
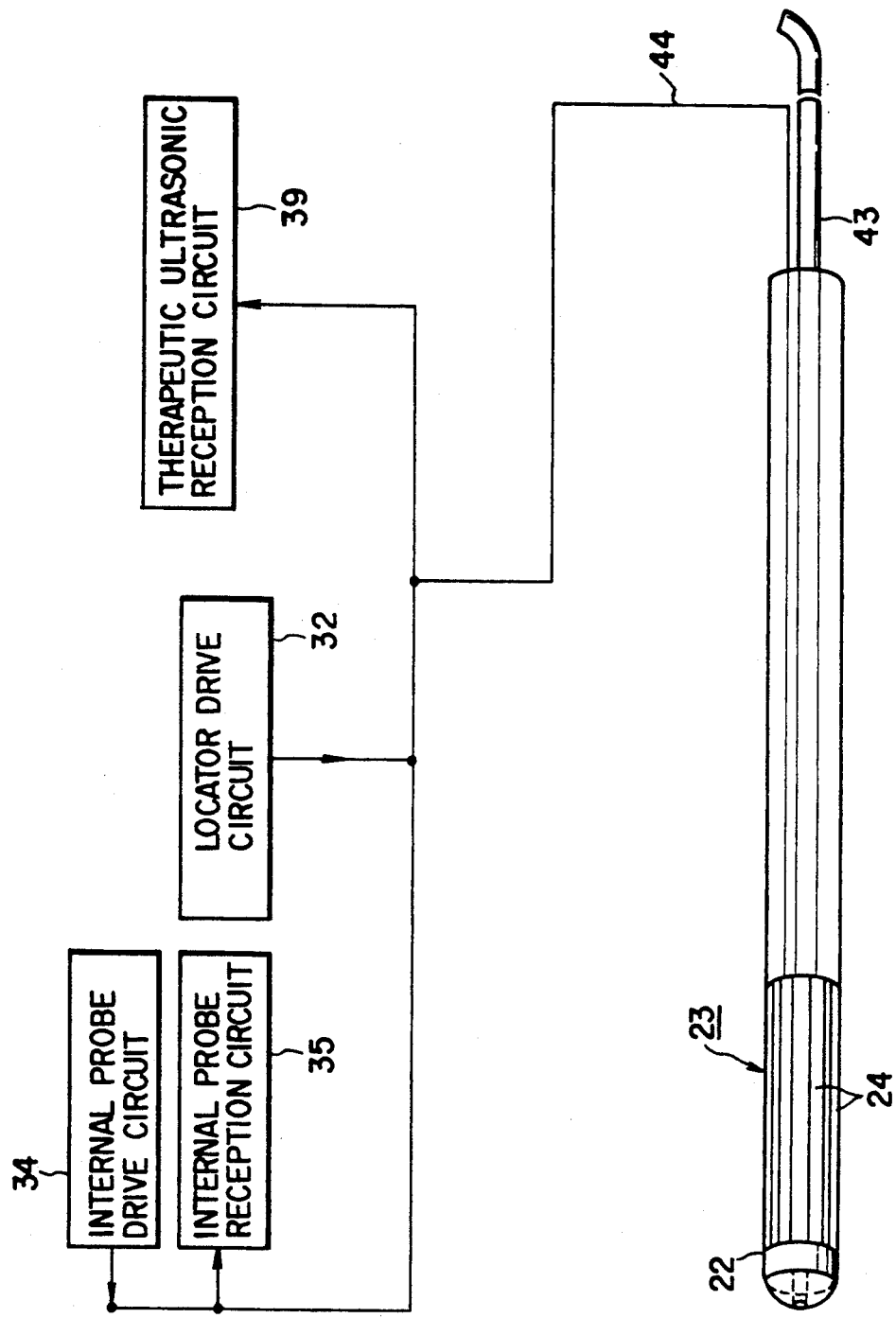
FIG. 2 is a view showing the main part of FIG. 1.

The ultrasonic transducer 23 will be described with reference to the perspective view of FIG. 2. A thrombus resolvent insertion tube 43 is inserted in the catheter 22, and the ultrasonic transducer 23 is connected to the respective constituent elements of the system body 25 through a cable 44. The ultrasonic transducer 23 of this embodiment is constituted by a vibrator array in which a plurality of strip-shaped (rectangular) piezoelectric elements 24 are arranged in the circumferential direction of the catheter 22 such that their longitudinal directions are aligned with the axial direction of the catheter 22.

Figure 3:
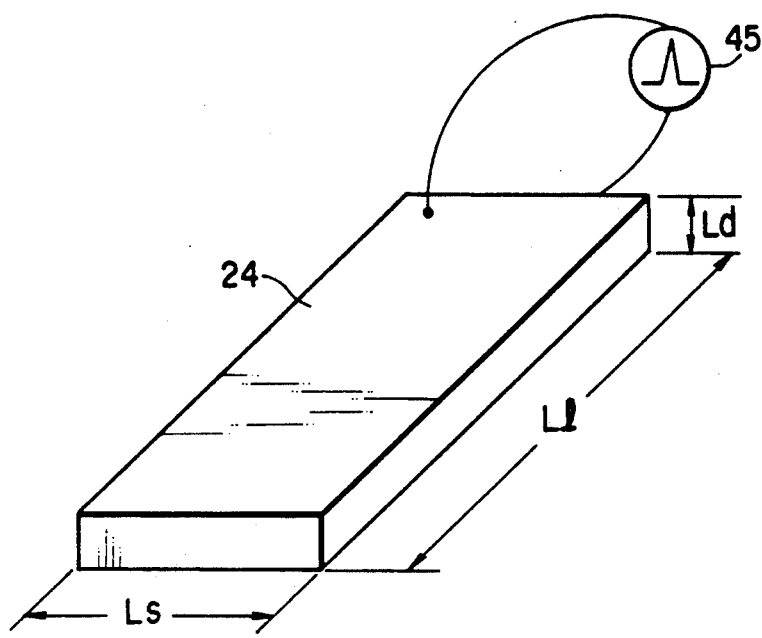
FIG. 3 is a view for explaining a piezoelectric element used in an ultrasonic transducer.

FIG. 3 is an enlarged perspective view of one strip-shaped piezoelectric element 24. Referring to FIG. 3, reference numeral 45 represents the internal probe drive circuit 34, the internal probe reception circuit 35, the locator drive circuit 32, and the therapeutic ultrasonic reception circuit 39 of FIG. 2 as a whole.

A thickness Ld, a length Ll, and a width Ls of the strip-shaped piezoelectric element 24 respectively correspond to an ultrasonic frequency for radial scanning to obtain tomographic image data on the blood vessel cross section as the first function of the transducer 23, a frequency (i.e., the frequency of the ultrasonic wave transmitted by the ultrasonic probe 21) of the ultrasonic transducer 23 as the locator which is the second function of the transducer 23, and a frequency of the therapeutic ultrasonic wave CUS received by the transducer 23 as the third function.

In the first embodiment, the ultrasonic frequency for so-called "radial scanning", the frequency of the ultrasonic wave transmitted by the ultrasonic probe 21, and the frequency of the therapeutic ultrasonic wave are 5 MHz, 20 MHz, and 450 kHz, respectively. Based on the relationship $\lambda/2 = d$ between a size d (any one of the thickness Ld, the length Ll, and the width Ls) of the piezoelectric element 24 in a certain direction and a wavelength $\lambda$ of the ultrasonic wave transmitted in those direction respectively in speed 3000 m/s, 2700 m/s and 1800 m/s, the thickness Ld, the width Ls, and the length Ll are respectively set to 0.075 mm, 0.27 mm, and 2 mm. Note that these dimensions can be changed to a certain degree even if the frequency is the same by changing the piezoelectric material (having a variety of strength characteristics) to be used.

As described above, according to the first embodiment, since the ultrasonic transducer 23 constituted by aligning only one type of piezoelectric elements 24 can serve all of the three functions described above, the number of piezoelectric elements and the entire volume are decreased, and one cable 44 suffices to connect the system body 25 and the ultrasonic transducer 23 to simplify the structure. As a result, the catheter 22 incorporating this ultrasonic transducer 23 can be easily inserted in a blood vessel when compared to a catheter in which three separate ultrasonic transducers are provided to execute the three functions described above.

Second Embodiment

Figure 4:
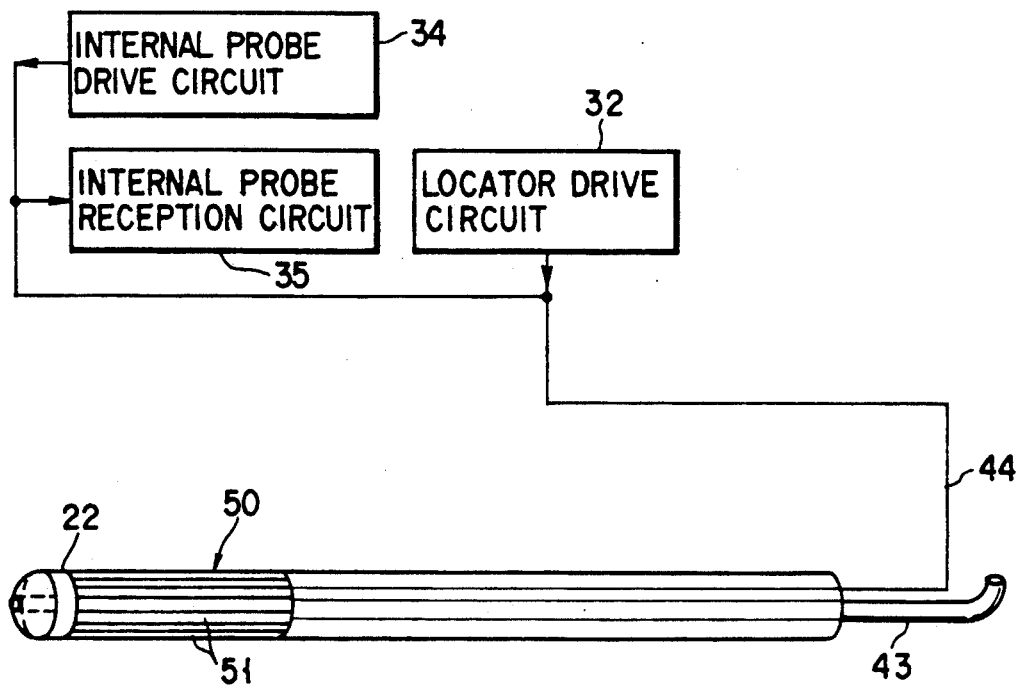
FIG. 4 is a view showing the structure of the main part according to the second embodiment of the present invention.

FIG. 4 is a perspective view of an ultrasonic transducer 50 according to the second embodiment of the present invention. When the therapeutic ultrasonic wave is not a convergent wave, its radiation position need not be monitored as it can hardly deviate from the thrombus. Hence, in the second embodiment, the constituent elements in the thrombus resolving apparatus of FIG. 1 concerning monitoring of the radiation position of the therapeutic ultrasonic wave are removed, and the ultrasonic transducer 50 is connected to this apparatus.

Regarding each of a plurality of strip-shaped piezoelectric elements 51 constituting the ultrasonic transducer 50, its thickness Ld may be matched to the ultrasonic frequency of radial scanning, and either one of its length Ll and width Ls may be matched to the frequency of the ultrasonic wave transmitted by an ultrasonic probe 21. Accordingly, this ultrasonic transducer 50 can be manufactured more easily.

The first and second embodiments exemplify an ultrasonic transducer constituted by vibrators for electronic scanning. However, a mechanical scanning type vibrator may also be employed in which only one strip-shaped piezoelectric element (its length, width, and thickness are matched to the target frequencies in accordance with the functions) is used, and this stripe-shaped piezoelectric element is rotated.

Third Embodiment

FIG. 5 shows the structure of a thrombus resolving treatment apparatus according to the third embodiment of the present invention. The most critical case worsened by thrombosis is an ischemic heart disease caused by a blood flow legion or blood flow occlusion in a coronary artery. In particular, since the coronary artery is surrounded by ribs, it is difficult to externally radiate a convergent therapeutic ultrasonic wave to a thrombus in the coronary artery. Hence, in the third embodiment, an ultrasonic transducer 60 mounted on a catheter 22 in the second embodiment is imparted with a function of radiating a therapeutic ultrasonic wave. The ultrasonic transducer 60 comprises a locator (can also be called a transponder) 62, a vibrator array (to serve as an internal ultrasonic probe) 63, and a therapeutic vibrator 64 which are mounted on the circumferential surface of the catheter 22 starting from the distal end in this order. The locator 62 and the therapeutic vibrator 64 are annular.

In the third embodiment, an ultrasonic beam having a center frequency of 3.75 MHz is radiated by an ultrasonic probe 21 and received by the locator 62. That is, the resonant frequency of each piezoelectric vibrator of the locator 62 is set to for example 3.75 MHz. A reception signal corresponding to the ultrasonic beam received by the locator 62 is sent to a locator reception circuit 65 to be amplified and detected, waveshaped to a rectangular wave by a waveshaper 66, and sent to a catheter position detection circuit 33 to obtain the position (distance and direction from the ultrasonic probe 21) of the locator 62.

The catheter position detection circuit 33 comprises a counter. When the ultrasonic probe 21 radiates the ultrasonic beam upon reception of a drive signal from the external probe drive circuit 26, the catheter position detection circuit 33 receives a trigger signal input to the external probe drive circuit 26 to start clock counting by its counter. The counter continues a count-up operation until a reception signal from the locator 62 is input. The position of the locator 62 is calculated from the count of the counter. The position data of the locator 62 is transferred to a tissue image system processing circuit 28. Simultaneously, the counter is reset to wait for the following position detection of the locator 62. The position data of the distal end of the catheter 22 input to the tissue image system processing circuit 28 is displayed on a tissue image CRT 29 in the form of a focal point or a marker as it is superposed on the B mode image of the internal tissues.

To detect the position of the locator 62, the locator 62 may be connected to a locator drive circuit, and the locator drive circuit may be connected to the waveshaper 66 in FIG. 5. That is, when there is an input to the waveshaper 66, the locator drive circuit is operated, and the locator 62 is caused to transmit an ultrasonic beam having a frequency of 3.75 MHz, which is the same as that of the frequency received by the locator 62. As a result, since this ultrasonic beam is received by the ultrasonic probe 21, the position of the locator 62 can be displayed on the tissue image CRT 29 when signal processing is performed to obtain the tomographic image of the internal tissues.

In the third embodiment, the vibrator array 63 generates an ultrasonic beam having a center frequency of 25 MHz and displays a cross-sectional image of the blood vessel 30 on a blood vessel B mode imaging CRT 37. The therapeutic vibrator 64 generates a therapeutic ultrasonic wave having a relatively low frequency of 450 kHz by radial resonance to resolve the thrombus 31 together with the thrombus resolvent. To administer the thrombus resolvent, a thrombus resolvent insertion tube may be inserted in the catheter 22 and the resolvent may be locally injected at the thrombus position from the distal end of the catheter 22. If the thrombus resolvent is the one which is reported to selectively act on the thrombus, like t-PA, the thrombus resolvent may be administered in accordance with intravenous drip.

Identification of the therapeutic effect, i.e., identification of the thrombus resolving state is performed in accordance with either one of the following two methods. According to one method, the recanalization rate of the blood vessel is obtained on the basis of the area occluded by a thrombus with respect to the cross-sectional area (i.e., tubular cavity area) of the cross-sectional image of the blood vessel displayed on the blood vessel B mode imaging CRT 37. When a predetermined recanalization rate is obtained in accordance with this method, administration of the thrombus resolvent or radiation of the therapeutic ultrasonic wave is stopped in accordance with the judgement of the operator. According to the other method, the blood flow in the thrombus portion is observed by a colored plamode, and the thrombus resolved state is identified from the degree of blood flow or the degree of legion in blood flow. In accordance with either method, the therapeutic ultrasonic wave is generated from the thrombus position in this embodiment. Hence, the therapeutic ultrasonic wave is precisely and reliably radiated on the thrombus to efficiently resolve the thrombus. Accordingly, this embodiment can be applied even to a disease in a coronary artery including a myocardial infarction, which is highly critical and must be treated urgently, to obtain a remarkable effect with a greatly shortened treatment time while propagation of the ultrasonic beam is not barred or disturbed by a rib or tissues in the vicinity of the body surface. Furthermore, the dosage of the thrombus resolvent can be minimized to prevent side effects.

In this embodiment, a ceramic or polymer is used as the material of the vibrator array 63. More specifically, examples of the ceramic are a lead zirconate titanate-based ceramic represented by PZT, a lead titanate-based ceramic, and a lead metaniobate-based ceramic, and examples of the polymer are polyvinyliden fluoride (PVDF), a copolymer of vinyliden fluoride (VDF) and ethylene trifluoride, and vinyliden cyanide. A piezoelectric composite consists of ceramic and polymer may also be used.

Fourth Embodiment

When a polymeric material is used for the ultrasonic transducer, since the ultrasonic transducer becomes a sheet, it needs to be wound on a catheter 22 and cannot be formed into a vibrator array. In this case, as in the fourth embodiment shown in FIG. 6, one internal ultrasonic probe vibrator 70 and a reflection plate 71 may be combined, and the reflection plate 71 may be rotated about the axis of the catheter 22 as indicated by an arrow 72 to perform radial scanning.

When radial scanning is to be performed by continuous Doppler waves, if the reflection plate described above is employed, different vibrators are needed for transmission and reception. Thus, for example, two resonators each for half the frequency may be connected and are used for transmission and reception, respectively.

If a locator 62, a vibrator array 63, and a therapeutic vibrator 64 are formed into a piezoelectric composite constituted by strip-shaped piezoelectric ceramics and resin both made of appropriate materials and alternately connected and aligned on the circumferential surface of a catheter, a single vibrator can serve as the locator 62, the vibrator array 63, and the therapeutic vibrator 64. In this case, the dimensions of the piezoelectric composite and the piezoelectric ceramics in respective directions may be appropriately determined, the radial resonance of the entire piezoelectric composite can be utilized for the therapeutic ultrasonic wave, the vibration in thickness of the piezoelectric ceramics perpendicular to the array direction can be utilized for the ultrasonic wave to observe the cross-sectional image of a blood vessel, and the resonance of the catheter in the axial direction can be utilized for the ultrasonic wave to indicate the position of the distal end of the catheter. Also, one vibrator can be set to have any two functions of the locator 62, the vibrator array 63, and the therapeutic vibrator 64.

Other Embodiments

Other embodiments of the present invention will be described with reference to FIGS. 7 to 14.

Figure 7:
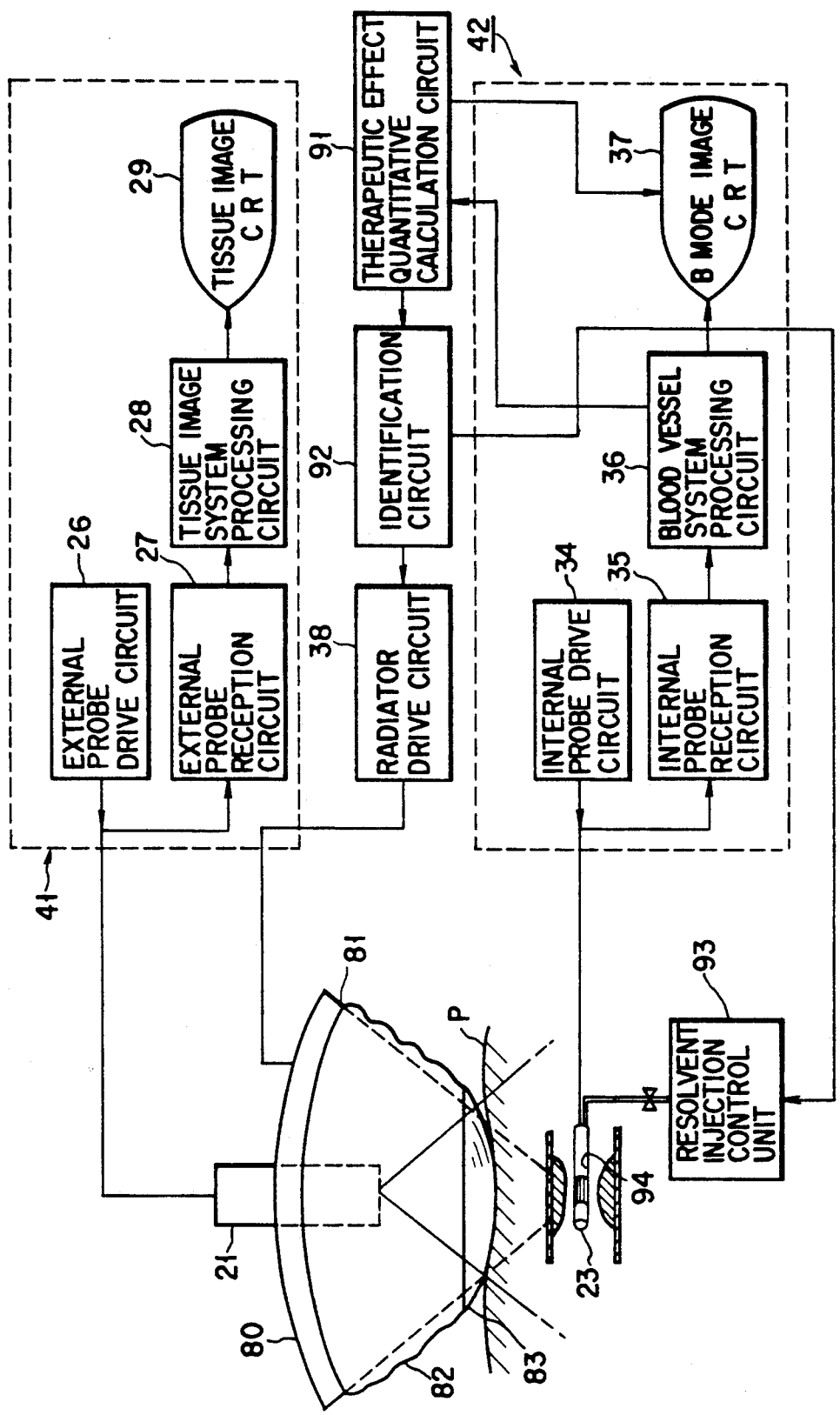
FIG. 7 is a view showing the structure of a thrombus resolving treatment apparatus according to the fifth embodiment of the present invention.

In the fifth embodiment, an ultrasonic radiator 80 for radiating a therapeutic ultrasonic wave comprises spherically arranged piezoelectric elements, as shown in FIG. 7. An acoustic matching layer 81 is applied on the front surface of the ultrasonic radiator 80, and a water bag 82 having a bellows is mounted on the matching layer 81. A film 83 which is to be brought into contact with the body surface of a patient P is mounted on the distal end of the water bag 82.

Figure 8:
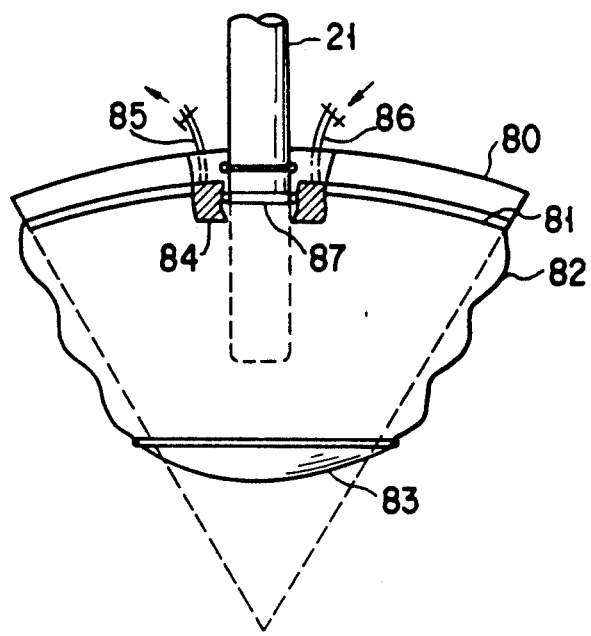
FIG. 8 is a view showing the structure of the main part of FIG. 7.
Figure 9:
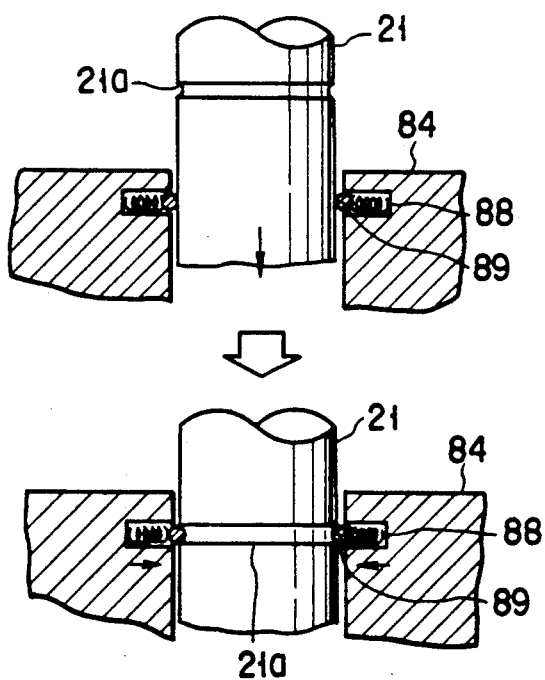
FIG. 9 is an enlarged view of the main part of FIG. 8.

As shown in FIG. 8, an ultrasonic probe 21 is detachably fixed to the ultrasonic radiator 80 through a tubular probe holding member 84. A packing 87 for keeping watertightness in the water bag 82 and fixing the ultrasonic radiator 80 and the ultrasonic probe 21 at predetermined positions is mounted on the holding member 84. The packing 76 comprises a spring 88 provided on the inner circumferential surface of the holding member 84 and an 0-ring 89 biased toward the center by the spring 88, as shown in FIG. 9. When the O-ring 89 enters a groove 21a formed at a predetermined position of the ultrasonic probe 21 along the circumferential direction, watertightness is maintained, and the ultrasonic radiator 80 and the ultrasonic probe 21 are fixed. A water inlet port 85 and a water outlet port 86 are connected to the water bag 82. Water is supplied to and discharged from the water bag 82 through the water inlet and outlet ports 85 and 86 to adjust the water quantity in the water bag 82. Then, the bellows is expanded or contracted to change the distance between the ultrasonic probe 21 and the body surface of the patient P, thereby changing the focal point of the probe 21 in the patient's body.

In FIGS. 7 and 8, the ultrasonic probe 21 is located at the central portion of the ultrasonic radiator Go. However, it may be located on a side of the central portion, as shown in FIG. 10. Also, an ultrasonic probe 21 may be externally fixed to an ultrasonic radiator 80 by a holding member 84, as shown in FIG. 11.

If an ultrasonic radiator 80 is constituted by using a so-called annular array type piezoelectric vibrator in which a plurality of annular vibrators are concentrically arranged, as shown in FIG. 12, the focal point can be electronically changed by driving the respective vibrators at different phases. Then, the water quantity in the water bag no longer need be increased or decreased, unlike in the embodiments described above, and thus the water bag can be replaced by a jelly pad 90. As a result, a water processing unit can be eliminated to improve the operability.

In the above description, any ultrasonic radiator 80 changes the focal point in the direction of depth. If a two-dimensional array type piezoelectric vibrator is used, as shown in FIG. 13, the focal point can be changed by electronic scanning, and thus the size of a jelly pad 90 can be further decreased, further improving the operability.

The waveform of the drive signal supplied from a radiator drive circuit 38 to the ultrasonic radiator 80 in FIG. 7 can be appropriately selected from a continuous wave, a burst wave, and a pulse wave shown in FIGS. 14(a) to 14(c). For example, if the thrombus portion as the treatment target is comparatively shallow and tissues, e.g., a bone or lung, that strongly reflect the ultrasonic wave to cause heat generation are not present in the propagation path of the therapeutic ultrasonic wave, a continuous wave is used. If the thrombus portion is deep and a bone or the like is present in the propagation path of the therapeutic ultrasonic wave so that each wave need to have a comparatively large energy, a pulse wave is used. In this manner, the waveform of the drive signal of the ultrasonic radiator 80 may be appropriately selected in accordance with the treatment conditions.

Referring back to FIG. 7, in the fifth embodiment, a therapeutic effect quantitative calculation circuit 91 is connected to a blood vessel B mode imaging system processing circuit 36. The calculation circuit 91 obtains the cross-sectional area of the blood vessel and the area of a portion in the blood vessel which is recanalized as the thrombus is resolved from image data of the cross section of the blood vessel obtained by the blood vessel B mode imaging system processing circuit 36 by image processing, thereby calculating the recanalization rate. The calculated recanalization rate is sent to a blood vessel B mode imaging CRT 37 and is numerically displayed.

Figure 15:
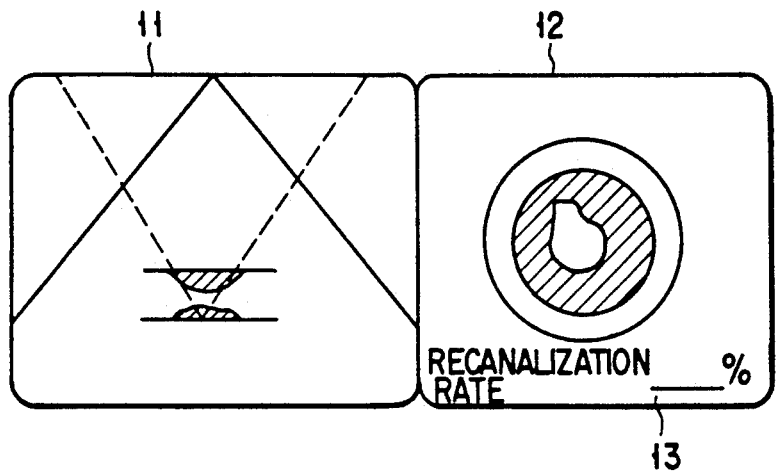
FIG. 15 shows display examples on a tissue image CRT and a blood vessel B mode imaging CRT according to the fifth embodiment of the present invention.

The recanalization rate is compared with a predetermined threshold value by an identification circuit 92. If the recanalization rate is larger than the threshold value, it is determined that the blood vessel is sufficiently recanalized and the treatment is completed, and the radiator drive circuit 38 is stopped to stop radiation of the therapeutic ultrasonic wave. In the fifth embodiment, when the identification circuit 92 determines that the treatment is completed, a resolvent injection control unit 93 is stopped to stop injection of the resolvent from a resolvent injection port 94 provided on the distal end portion of a catheter 22 into the blood vessel. The resolvent injection control unit need not be of a type to inject the resolvent from the distal end of the catheter but can be of a drip type. FIG. 15 shows display examples on a tissue image CRT 29 and a blood vessel B mode imaging CRT 37. The tissue image CRT 29 displays a B mode image 11 of the interior of the patient P. The blood vessel B mode imaging CRT 37 displays an image 12 of the cross section of the blood vessel and the recanalization rate as indicated by reference numeral 13. In this manner, since not only the B mode tomographic image 11 but also the blood vessel cross-sectional image 12 and the recanalization rate 13 are displayed, the recanalization degree of a blood vessel, which is hard to be determined from only the M mode image and can be confirmed by only X-ray fluoroscopy, can be clearly and quantitatively obtained, making it possible to give suggestions to the determination of the therapeutic effect. In particular, if the recanalization rate is quantitatively obtained by the calculation circuit 91 and compared with the threshold value by the identification circuit 92, the thrombus resolving treatment can be automatically stopped, as described above.

Figure 16A:
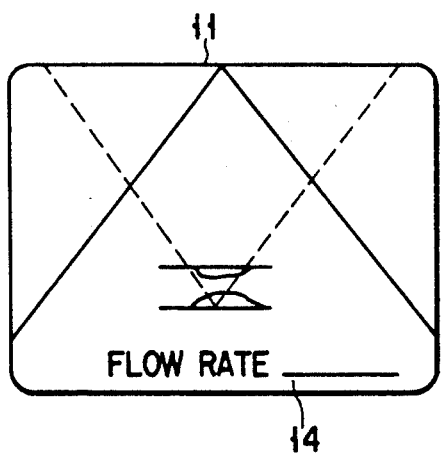
FIGS. 16A and 16B are views showing display examples on the tissue image CRT.
Figure 16B:
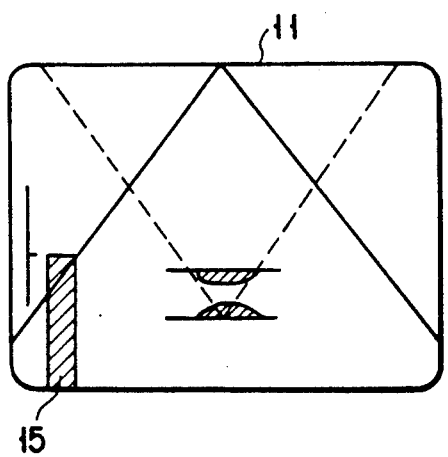

In this embodiment, cross-sectional image data of the blood vessel is obtained to determine the recanalization state of the blood vessel. However, a Doppler catheter may be used to measure the blood flow in the blood vessel, thereby determining whether the blood vessel is recanalized or not. In this case, when a numerical display 14 of the flow rate is added to a B mode tomographic image 11, as shown in FIG. 16A, or when a bar graph 15 is displayed, as shown in FIG. 16B, the operator can determine the therapeutic effect more easily.

Furthermore, it is also possible to directly monitor the interior of the blood vessel by blood vessel B mode imaging using an optical fiber, thereby obtaining the recanalization state of the blood vessel.

According to the present invention, the thrombus portion can be confirmed by displaying the tomographic image of the interior of the patient by the first ultrasonic imaging unit, and the state of the thrombus resolving treatment can be obtained by displaying the tomographic image of the blood vessel by the second ultrasonic imaging unit. Therefore, a therapeutic ultrasonic wave can be radiated precisely to the thrombus portion to improve the therapeutic effect, and when the thrombus is sufficiently resolved, excessive administration of the thrombus resolvent is prevented to avoid undesirable side effects.

A value, e.g., a blood vessel recanalization rate, that represents the effect of the thrombus resolving treatment is obtained by calculation. When this value has reached a predetermined value, radiation of the therapeutic ultrasonic wave by the ultrasonic radiator is stopped, and furthermore injection of the thrombus resolvent into the blood vessel is stopped, thereby automatically stopping the treatment when the thrombus is sufficiently resolved. As a result, a more efficient treatment having less side effects is enabled.

Furthermore, a therapeutic ultrasonic wave from the ultrasonic probe is detected by the ultrasonic transducer inserted in the blood vessel to detect the position of the catheter, and the detection result is displayed to be superposed on the tomographic image of the interior of the patient's body, so that whether or not the catheter is correctly inserted in the thrombus portion can be confirmed. In this case, one strip-shaped piezoelectric element can be set to serve two functions, i.e., a function of monitoring the blood vessel tomographic image and a function of detecting the catheter position by appropriately selecting the sizes of the strip-shaped piezoelectric element used in the ultrasonic transducer. As a result, the size of the transducer is reduced, and the transducer can be easily mounted on the catheter.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. A thrombus resolving treatment apparatus for resolving a thrombus by radiating a therapeutic ultrasonic wave on a thrombus portion located in a blood vessel of a patient's body in which a thrombus resolvent is injected, comprising:

an ultrasonic radiator for radiating a therapeutic ultrasonic wave on said thrombus portion;

an ultrasonic probe for obtaining tomographic image data of an interior of said patient's body;

a first ultrasonic imaging unit for visually displaying the tomographic image data supplied from said ultrasonic probe;

a catheter which is inserted into said blood vessel;

an ultrasonic transducer, mounted on said catheter, for obtaining tomographic image data of an interior of said blood vessel; and a second ultrasonic imaging unit for visually displaying the tomographic image data supplied from said ultrasonic transducer;

said apparatus further comprising:

calculation means for calculating a value representing an effect of a thrombus resolving treatment on the basis of the tomographic image data supplied from said ultrasonic transducer;

identification means for identifying whether or not said value has reached a predetermined value; and means for stopping radiation of the therapeutic ultrasonic wave by said ultrasonic radiator when the value calculated by said calculation means has reached said predetermined value.

2. The apparatus according to claim 1, wherein said calculation means is connected to said identification means, and said apparatus further comprises injection control means, connected to said identification means, for controlling the injection of the thrombus resolvent into said blood vessel on the basis of a predetermined signal generated by said identification means.

3. The apparatus according to claim 1, wherein said ultrasonic radiator comprises spherically arranged piezoelectric elements, an acoustic matching layer being applied on a front surface of said ultrasonic radiator, a water bag having a bellows being mounted on said acoustic matching layer, and a film to be brought into contact with a body surface of the patient being mounted on a distal end of said water bag.

4. The apparatus according to claim 1, wherein said ultrasonic probe is detachably fixed to said ultrasonic radiator by a tubular probe holding member, and mounted on said ultrasonic radiator when a packing for maintaining watertightness of said water bag and for fixing said ultrasonic radiator and said ultrasonic probe at predetermined positions is fitted in a groove formed at a predetermined position of said ultrasonic probe along a circumferential direction by spring means provided on an inner circumferential surface of said holding member and ring means biased toward a center of said holding member.

5. The apparatus according to claim 3, wherein said ultrasonic radiator is constituted by an annular array type piezoelectric vibrator in which a plurality of annular vibrators are concentrically located, and each of said vibrators electronically changes a focal point at different phases.

6. The apparatus according to claim 3, wherein said ultrasonic radiator is a two-dimensional array type piezoelectric vibrator.

7. The apparatus according to claim 1, wherein said ultrasonic probe is stationarily disposed at a central or peripheral portion of said ultrasonic radiator.

8. A thrombus resolving treatment apparatus for resolving a thrombus by radiating a therapeutic ultrasonic wave on a thrombus portion located in a blood vessel of a patient's body in which a thrombus resolvent is injected, comprising:

an ultrasonic radiator for radiating a therapeutic wave on said thrombus portion;

an ultrasonic probe for obtaining tomographic image data of an interior of said patient's body;

a first ultrasonic imaging unit, connected to said ultrasonic probe, for visually displaying the tomographic image data supplied from said ultrasonic probe;

a catheter which is inserted into said blood vessel;

an ultrasonic transducer, mounted on said catheter, for obtaining tomographic image data of an interior of said blood vessel; and a second ultrasonic imaging unit, connected to said ultrasonic transducer, for visually displaying the tomographic image data supplied from said ultrasonic transducer;

wherein said ultrasonic radiator is mounted on said catheter.

9. A thrombus resolving treatment apparatus for resolving a thrombus by radiating a therapeutic ultrasonic wave on a thrombus portion located in a blood vessel of a patient's body in which a thrombus resolvent is injected, comprising:

an ultrasonic radiator for radiating a therapeutic ultrasonic wave on said thrombus portion;

an ultrasonic probe for obtaining tomographic image data of an interior of said patient's body by transmitting and receiving an ultrasonic wave having a predetermined frequency;

a first ultrasonic imaging unit, connected to said ultrasonic probe, for visually displaying the tomographic image data supplied from aid ultrasonic probe;

a catheter which is inserted into said blood vessel;

an ultrasonic transducer, mounted on said catheter, for obtaining tomographic image data of an interior of said blood vessel by transmitting and receiving an ultrasonic wave having a frequency different from that of the ultrasonic wave transmitted and received by said ultrasonic probe, and for detecting the ultrasonic wave transmitted from the ultrasonic probe, wherein said ultrasonic transducer comprises at least one strip-shaped piezoelectric element provided along a longitudinal direction of said catheter and having the dimensions of thickness, length in a circumferential direction of said catheter, and length in an axial direction of said catheter, any two of said dimensions being selected so as to correspond to a frequency of the ultrasonic wave transmitted from and received by said ultrasonic transducer and to a frequency of the ultrasonic wave transmitted from and received by said ultrasonic probe, respectively, and wherein the remaining dimension of said piezoelectric element is selected so as to correspond to a frequency of the ultrasonic wave radiated by said ultrasonic radiator;

a second ultrasonic imaging unit, connected to said ultrasonic transducer, for visually displaying the tomographic image data supplied from said ultrasonic transducer;

position detection means, connected to said ultrasonic transducer, for processing an ultrasonic wave signal output from said ultrasonic probe upon receipt from said ultrasonic transducer, thereby detecting a position within said blood vessel of said catheter; and means for displaying a detected result of said position detection means on a display screen of said first ultrasonic imaging unit.

* * * * *